US006525035B1

(12) United States Patent
Danilov et al.

(10) Patent No.: US 6,525,035 B1
(45) Date of Patent: Feb. 25, 2003

(54) THERAPEUTIC COMPOSITION AND METHODS

(75) Inventors: Leonid L. Danilov, Moscow (RU);
Anna V. Deeva, Moscow (RU); Tanya Kuritz, Kingston, TN (US); Sergei D. Maltsev, Moscow (RU); Alexander N. Narovlianskiy, Moscow (RU);
Alexander V. Pronin, Moscow (RU);
Alexander V. Sanin, Moscow (RU);
Olga Y. Sosnovskaya, Moscow (RU);
Sergei V. Ozherelkov, Moscow (RU)

(73) Assignee: Sass & Sass, Inc., Kingston, TN (US)

( * ) Notice: Subject to any disclaimer, the term of this patent is extended or adjusted under 35 U.S.C. 154(b) by 0 days.

(21) Appl. No.: 09/329,808

(22) Filed: Jun. 10, 1999

(51) Int. Cl.$^7$ ............................................... A61K 31/66

(52) U.S. Cl. ...................... 514/106; 514/143; 514/134; 514/102; 514/75

(58) Field of Search .................. 514/75, 102, 106, 514/134, 143

(56) References Cited

U.S. PATENT DOCUMENTS 4,613,593 A * 9/1986 Yamatsu et al. ............. 514/106

FOREIGN PATENT DOCUMENTS

| EP | 0166436 | 1/1986 | ........... C70C/33/02 |
| EP | 0350801 | 1/1990 | ......... A61K/34/045 |
| RU | 2005475 | 10/1991 | |

OTHER PUBLICATIONS

CAPlus Abstract, AN 1989:20110, 1989, Janas et al.*
CAPlus Abstract AN 1995:728714, 1995, Mal'tsev et al.*
"Against Distemper and Enteritis: Phosprenyl", *Cat & Dog Magazine, 11,* Interview With A. V. Deeva, 1 p., (1996).
"Twelve Reasons Why You Should Immediately Get Phosprenyl—A New Generation Antiviral Drug", *Cat & Dog Magazine,* Russia, 1 p., (1997).
"Phosrenyl—Viruses Give Up", *Coupon,* Abstracts of Interviews and Papers From Russian Language Sources, 1 p., (1996).
Danilov, L.L., et al., "Phosprenyl: A Novel Drug With Antiviral and Immunomodulatory Activity." *Archivum Immunologiae et Therapiae Experimentalis, 44,* pp. 395–400, (1996).
Deeva, A.V., et al., "Phosprenyl– A Broad Spectrum Antiviral Preparation", *Veterinary Practice, 1(4),* pp. 12–22, (1998).
Deeva, A.V., et al., "Phosprenyl– A Broad Spectrum Antiviral Preparation", *Veterinarian, 3,* pp. 15–21, (1998).
Narovlyansky, A.N., et al., "Cytokine RNA Profile in Cell Line MG–63 With and Without Induction With Phosprenyl and Kagocel", *European Cytokine Network, 9 (3),* Abstract No. 177, p. 515, (Sep. 1998).

Narovlyansky, A.N., et al., "Phosprenyl– Antiviral Drug With Interferon–Inducing and Immunomodulatory Activities.", *Abstracts of the First Joint Meeting of the International Cytokine Society and International Society for Interferon and Cytokine Research.,* Abstract No. 186, Amsterdam, The Netherlands, p. 502, (1996).
Narovylansky, A.N., et al., "The Influence of Phosprenyl Upon the Action of Interferon Inducers.", *European Cytokine Network, 9(3),* Abstract No. 330, p. 435, (Sep. 1998).
Ozherelkov, S.V., et al., "Enemies of our Friends", *Cat & Dog Magazine, 11,* 1 p., (1997).
Ozherelkov, S.V., et al., "Methods for Prevention of Viral Infections", *Cat & Dog Magazine, 10,* 1 p., (1997).
Ozherelkov, S.V., et al., "Phosprenyl Against Viral Infections in Cats", *Bird Market Magazine, 18, 19,* 1 p., (1997).
Pronin, A., et al., "Depot–Form of Phosphopolyprenols as Protective Remedy for Influenza.", *Abstracts of "Options for the Control of Influenza",* Cairns, Australia, Abstract No. P1–11, (1996).
Pronin, A.V., "Attack on Viruses– Interview With Dr. Pronin", *Veterinary Gazette, 8,* 1 p., (1996).
Pronin, A.V., et al., "Phosprenyl: A Novel Drug Active Against Animal and Human Viruses", *Abstract of the First Congress of the European Society for Emerging Infections, Poster 28,* Budapest, Hungary, p. 98, (Sep. 13–16, 1998).
Pronin, A.V., et al., "Protective Actions of the New Preparation Phosprenyl in Some Human Experimental Viral Infections", *Abstract of the 1st National Conference of the Russian Association of Allergologists and Clinical Immunologists,* Moscow, Russia, p. 73, (Jan. 28–31, 1997).
Sanin, A.V., "Again, About Phosprenyl", *Cat & Dog Magazine, 6(68),* 1 p., (1996).
Sanin, A.V., "Viruses are no Threat to Phosprenyl", *Cat & Dog Magazine, 3(65),* 1 p., (1996).
Sanin, A.V., et al., "If You do not Have a Dog . . . ", *Cat & Dog Magazine, 6(80),* 1 p., (1997).
Sanin, A.V., et al., "If You do not Have a Dog. . . (continued)", *Cat & Dog Magazine, 7(81),* 1 p., (1997).

(List continued on next page.)

Primary Examiner—Russell Travers
Assistant Examiner—Shengjun Wang
(74) Attorney, Agent, or Firm—Schwegman, Lundberg, Woessner & Kluth, P.A.

(57) ABSTRACT

The invention provides composition comprising, 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof, which is useful as an antiviral agent, as an immunomodulatory agent, and for treating cancer. The invention also provides pharmaceutical compositions comprising the compositions of the invention as well as therapeutic methods for using the the compositions.

22 Claims, No Drawings

OTHER PUBLICATIONS

Sanin, A.V., et al., "Inhibition of HIV–1 in Vitro Infectivity by a P16 Substance With a Potent Antiviral Activity.", *Abstracts of the VIII International Conference on AIDS STD World Congress.*, Amsterdam, The Netherlands, Abstract No. PuA 6149, (Jul. 19–24, 1992).

Sanin, A.V., et al., "New Immunomodulators of Natural Origin for Therapy of Acute Viral Infections", *Abstracts of the Meeting "Dolichol and Related Lipids"*, Zakopane, Poland, p. 151, (Aug. 11–13, 1993).

Sanin, A.V., et al., "Phosprenyl Against Viruses", *Animal World Magazine, 1,* 1 p., (1997).

Sanin, A.V., et al., "Phosprenyl—A Novel Stimulation of Natural Resistance", *European Cytokine Network, 9 (3),* Abstract No. 466, p. 537, (Sep. 1998).

Shibaev, V.N., et al., "New Developments in the Synthesis of Phosphopolyprenols and Their Glycosyl Esters.", *Biochemical, Cellular Biology, 70,* pp. 429–437, (1992).

* cited by examiner

THERAPEUTIC COMPOSITION AND METHODS

PRIORITY OF INVENTION

This application claims priority of invention under 35 U.S.C. §119 from Russian Patent Number 2129867 filed Jun. 10, 1998, and allowed May 10, 1999.

BACKGROUND OF THE INVENTION

Russian patent number 2005475 (1994) discloses compositions comprising polyprenil phosphate which are reported to possess antiviral activity.

L. L. Danilov, et al., *Archivum Immunologiae and Thrapiae Experimentalis*, 1996, 44, 395–400 disclose a polyprenyl phosphate composition (PHOSPRENYL) that has antiviral and immunomodulatory activity. A. N. Narovlyansky, et al., Abstracts of the Second Joint Meeting of the International Cytokine Society and International Society for Interferon and Cytokine research, Jerusalem, Israel, Oct. 25–30 1998, and A. V. Sanin, et al., Abstracts of VII International Conference on AIDS, Amsterdam, the Netherlands, Jul. 19–24, 1992, also describe similar biological activity for PHOSPRENYL.

A. V. Sanin, et al. Abstracts of the meeting "Dolichols and Related Lipids", Aug. 11–13, 1993, Zakopane, Poland, disclose a phosphorylated polyisoprenoid composition P16 that is reported to be a novel immunomodulatory agent and antiviral drug that might be promising in immunotherapy of infectious diseases. The composition is reported to modulate NK activity, enhance X-ray resistance, modulate GM-CSF levels, stimulate hematopoietic stem cell migration, stimulate interferon activity, and to possess mild adjuvant activity. The composition is also disclosed to possess a strong dose-dependent inhibitory activity against HIV-1 infection in MT4 cells, and to inhibit hepatitis A virus, bovine leukemia virus, adenovirus, and tick encephalitis.

Additionally, European Patent Application 0 350 801 discloses polyprenols and polyprenyl phosphates that are useful for the inhibition of tumor metastasis.

Despite the above disclosures, there is currently a need for additional therapeutic agents with antiviral and immunomodulatory activity. In particular, there is a need for agents that have improved activity or improved physical characteristics compared to known agents. For example, the PHOSPRENYL composition identified above is limited for therapeutic purposes by a low solubility in water and other polar solvents.

SUMMARY OF THE INVENTION

Applicant has discovered certain compositions that are useful for the prevention, treatment, and liquidation of consequences of diseases, including viral, chlamidial, bacterial related diseases, oncology related diseases, diseases related to the liver, gastrointestinal, urologic and reproductive systems, and diseases related to the function of the immune system. The compositions are also useful in the treatment of wounds, burns, and stresses, and are useful for medical (human) and veterinary applications. The pyrophosphate containing compositions of the invention have improved solubility compared to related known compositions, and as a result, demonstrate improved levels of activity against certain diseases.

Accordingly, the invention provides a composition comprising, 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive, or a salt thereof.

The invention also provides a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive, or a salt thereof.

The invention also provides a pharmaceutical composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof; and a pharmaceutically acceptable carrier.

The invention also provides a pharmaceutical composition comprising polyprenol pyrophosphates of the formula H—[—CH2-C(CH3)=CH—CH$_2$]$_m$—O—P(=O)(OH)—O—P(=O) (OH)$_2$ wherein m is an integer from 6–19 inclusive, or a salt thereof; and a pharmaceutically acceptable carrier.

The invention also provides a method for producing an antiviral effect in an animal comprising administering to an animal in need of such treatment, an effective antiviral amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH2]$_m$—O—P(=O)(OH)—O—P(=O)(OH)$_2$ wherein m is an integer from 6–19 inclusive or a salt thereof. As used herein "animal" includes for example mammals (e.g. a dog, cow, cat, or human), birds (e.g. poultry), and other animals that can effectively be treated with the compositions of the invention.

The invention also provides a method for producing an antiviral effect in an animal comprising administering to an animal in need of such treatment, an effective antiviral amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for modulating (e.g. normalizing or upregulating) the immune system of an animal comprising administering to an animal in need of such treatment, an effective immunomodulatory amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for modulating (e.g. normalizing or upregulating) the immune system of an animal comprising administering to an animal in need of such treatment, an effective immunomodulatory amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for the treatment of disease caused by distemper virus (DV), canine enteritis (parvo, rota, and corona viruses; CEV), canine infectious hepatitis (CIH), feline infectious gastroenteritis (panleukopenia, FIE), feline infectious rhinotracheitis (agent—herpes virus; FIR), feline infectious enteritis and peritonitis (agent—corona virus, FIP), swine transmissive gastroenteritis (agent—rotavirus; STG), murine ectromelia (ME), cattle leukemia (CL), calf mixed viral infection (agents—parvo, adeno, and corona viruses; CMVI), western equestrian encephalomyelitis (WEE), or rabies (RV), comprising administering to an animal in need of such treatment, an effective therapeutic amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for the treatment of distemper virus (DV), canine enteritis (parvo, rota, and corona viruses; CEV), canine infectious hepatitis (CIH), feline infectious gastroenteritis (panleukopenia, FIE), feline infectious rhinotracheitis (agent—herpes virus; FIR), feline infectious enteritis and peritonitis (agent—corona virus, FIP), swine transmissive gastroenteritis (agent—rotavirus; STG), murine ectromelia (ME), cattle leukemia (CL), calf mixed viral infection (agents—parvo, adeno, and corona viruses; CMVI), western equestrian encephalomyelitis (WEE), or rabies (RV), comprising administering to an animal in need of such treatment, an effective therapeutic amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for upregulating the Th1 (cell immunity) system in an animal comprising administering to an animal in need of such treatment, an effective amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for upregulating the Th1 (cell immunity) system in an animal comprising administering to an animal in need of such treatment, an effective amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method for enhancing the protective effects of a vaccine comprising administering the vaccine to an animal in need of such treatment in combination with an amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof, effective to enhance the effect of the vaccine. As used herein, "enhansing the effect of a vaccine" means increasing the protective effect of the vaccine by a significant and measureable amount.

The invention also provides a method for enhancing the protective effects of a vaccine comprising administering the vaccine to an animal in need of such treatment in combination with an amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof, effective to enhance the effect of the vaccine.

The invention also provides a method to correct an individual immune system comprising administering to an animal in need of such treatment, an effective amount of a composition comprising 1) polyprenol monophosphates of the formula H—[—CH2-C(CH3)=CH—CH2]n-O—P(=O)(OH)2 wherein n is an integer from 6–19 inclusive or a salt thereof, and 2) polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

The invention also provides a method to correct an individual immune system comprising administering to an animal in need of such treatment, an effective amount of a composition comprising polyprenol pyrophosphates of the formula H—[—CH2-C(CH3)=CH—CH$_2$]$_m$—O—P(=O)(OH)—O—P(=O)(OH)$_2$ wherein m is an integer from 6–19 inclusive or a salt thereof.

DETAILED DESCRIPTION

It will be appreciated by those skilled in the art that polyprenes possess double bonds which may exist in cis, or trans configurations. It is to be understood that the present invention encompasses any stereoisomeric form of the polyenes as well as mixtures thereof, which possess the useful properties described herein.

Specific and preferred values listed below are for illustration only; they do not exclude other defined values or other values within defined ranges for the radicals and substituents.

A specific composition of the invention is a composition wherein n is at least 7, wherein the polyprenol monophosphate comprises at least 90% of the weight of the composition and the and polyprenol pyrophosphate comprises less 10% of the weight.

A specific composition of the invention is a composition wherein n is 9, 10, 11, 12, 13, or 14 in greater than 50% of the polyprenol monophosphates.

A specific composition of the invention is a composition wherein m is 9, 10, 11, 12, 13, or 14 in greater than 50% of the polyprenol pyrophosphates.

A specific composition of the invention is a composition wherein the weight percent of polyprenol monophosphates is greater than the weight percent of the polyprenol pyrophosphates.

A specific composition of the invention is a composition wherein the weight percent of polyprenol monophosphates is not more than about 2 times greater than the weight percent of the polyprenol pyrophosphates.

A specific composition of the invention is a composition wherein the weight percent of polyprenol monophosphates is not more than about 4 times greater than the weight percent of the polyprenol pyrophosphates.

A specific composition of the invention is a composition wherein the weight percent of polyprenol monophosphates is not more than about 5 times greater than the weight percent of the polyprenol pyrophosphates.

A specific composition of the invention is a composition wherein the weight percent of polyprenol monophosphates is not more than about 10 times greater than the weight percent of the polyprenol pyrophosphates.

A specific composition of the invention is a composition wherein the weight percent of polyprenol monophosphates is not more than about 20 times greater than the weight percent of the polyprenol pyrophosphates.

A specific composition of the invention is a composition wherein n is 11 in at least 80% of the polyprenol monophosphates present.

A specific composition of the invention is a composition wherein m is 11 in at least 80% of the polyprenol pyrophosphates present.

A specific composition of the invention is a composition wherein n is 11 in at least 80% of the polyprenol monophosphates present, and m is 11 in at least 80% of the polyprenol pyrophosphates present.

A specific composition of the invention is a composition wherein n is 11 in at least 80% of the polyprenol monophosphates present, m is 11 in at least 80% of the polyprenol pyrophosphates present, and the weight percent of polyprenol monophosphates is about 10 times greater than the weight percent of the polyprenol pyrophosphates.

A specific composition of the invention is a composition wherein n is 11 in at least 90% of the polyprenol monophosphates present.

A specific composition of the invention is a composition wherein m is 11 in at least 90% of the polyprenol pyrophosphates present.

A specific composition of the invention is a composition wherein n is 11 in at least 90% of the polyprenol monophosphates present, and m is 11 in at least 90% of the polyprenol pyrophosphates present.

A specific composition of the invention is a composition wherein n is 11 in at least 90% of the polyprenol monophosphates present, m is 11 in at least 90% of the polyprenol pyrophosphates present, and the weight percent of polyprenol monophosphates is about 10 times greater than the weight percent of the polyprenol pyrophosphates.

It is to be understood that specific compositions of the invention can also comprise up to about 10 percent by weight unphosphorylated polyprenols.

The polyprenol phosphates and pyrophosphates can be prepared from polyprenol using procedures similar to those known in the art. For example see V. N. Shibaev, and L. L. Danilov, *Biochem. Cell Biol.,* 1992, 70, 429–437 and European Patent Application Number 0 350 801.

Polyprenols can be isolated from natural sources using procedures similar to those described by, Danilov L. L. and Shibaev V. N. (1991): Phosphopolyprenols and their glycosyl esters: chemical synthesis and biochemical application, Atta-ur-Rahman (ed): Studies in natural products chemistry, Elsevier, Amsterdam—Oxford—New York—Tokyo, 8, 63–114; T. Choinacki, *Acta. Chem. And Biochem Polonica,* 1984, 21, 3–25; and F. Takaki et al., European Patent Application 0166436A2.

Administration of the compounds as salts may be appropriate. Examples of acceptable salts include alkali metal (for example, sodium, potassium or lithium) or alkaline earth metal (for example calcium) salts, however, any salt that is non-toxic and effective when administered to the animal being treated is acceptable.

Acceptable salts may be obtained using standard procedures well known in the art, for example by reacting a sufficiently acidic compound with a suitable base affording a physiologically acceptable anion.

The compositions of the invention can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. When administered orally, the compositions of the invention can preferably be administered in a gelatin capsule.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be from about 0.1–50 wt-%, preferably from about 0.5–5 wt %. The concentration in a semi-solid or solid composition such as a gel or a powder will be about 0.1–5 wt-%, preferably about 0.5–2.5 wt-%.

The amount of the composition required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compositions of the invention are poly-functional both at the cellular and at the organism levels. At the cellular level, they are incorporated in cellular membranes, enhancing their permeability. They also normalize and activate processes of cell surface glycoprotein biosynthesis, normalizing cell reproduction intracellular, and, as a result, intertussue interactions. In the organism on the whole they normalize immune system functioning, improve the function of individual organs, enhances blood generation function, and facilitate tissue regeneration.

The compositions of the invention are useful for prevention, treatment and liquidation of consequences of diseases, including viral, clamidial, bacterial, oncology, liver, gastrointestinal, urologic and reproductive system, immune system, wounds, burns, and stresses.

Following i.m. administration, the compositions of the invention enter the blood stream within about 10–15 minutes and reach a maximum concentration in the blood within one hour of administration, at which point they can be found throughout the circulatory related organs.

The antiviral activity of the compositions of the invention can be determined using assays that are known in the art, or can be determined using assays similar to those described in the following examples.

The compositions of the invention can be used for the treatment of animal diseases caused by numerous viruses including distemper virus (DV), canine enteritis (parvo, rota, and corona viruses; CEV), canine infectious hepatitis (CIH), feline infectious gastroenteritis (panleukopenia, FIE), feline infectious rhinotracheitis (agent—herpes virus; FIR), feline infectious enteritis and peritonitis (agent—corona virus, FIP), swine transmissive gastroenteritis (agent—rotavirus; STG), murine ectromelia (ME), cattle leukemia (CL), calf mixed viral infection (agents—parvo, adeno, and corona viruses; CMVI), western equestrian encephalomyelitis (WEE), and rabies (RV).

As used in the examples hereinbelow, "the Substance" is a composition of the invention wherein n is II in at least 80% of the polyprenol monophosphates present, m is 11 in at least 80% of the polyprenol pyrophosphates present, and the weight percent of polyprenol monophosphates is about 10 times greater than the weight percent of the polyprenol pyrophosphates.

EXAMPLE 1

Effect on DV

DV sensitive cell culture 4647 was infected with Strain Rockborn; simultaneously with the virus, the Substance was introduced into the flask in the doses of 20 and 200 ug/ml. Into the cell monolayer in 50-ml flasks applied was 0.1 ml of DV with the titer of 2.4 lg PFU (Plague Forming Units)/ml, incubated at +34° C. for 2 h (adsorption period), after which agar layer was applied. Before the application of agar, it was mixed with the Substance to final concentrations of 20 and 200 µg/ml. Cultures treated by the Substance in the same concentrations (without DV) served as toxicity controls. The experiments were repeated three times. Mean results are presented in Table 1.

| Substance concentration, µg/ml | DV titer, 1 g PFU/ml | Toxicity |
| --- | --- | --- |
| 0 | 4.18 | None |
| 20 | 3.20 | None |
| 200 | 0 | None |

Thus, the Substance has a high, dose-dependent inhibitory effect to DV. 100% inhibitory effect is observed with the Substance dose 200 µg/ml.

EXAMPLE 2

Therapeutic Evaluation of the Substance Activity in Distemper in Dogs

To evaluate therapeutic activity of the Substance, a model of distemper in dogs of Tibetan Terrier breed (12–13 weeks of age) was used. Experimental (5 animals) and control (5 animals) dogs were infected with DV (Snyder-Hill strain) intracerebrally with 50 $LD_{50}$ in 0.3 ml. Control group puppies were treated according to standard symptomatic treatment plan. Experimental dogs, along with symptomatic treatment, were injected intramuscularly with the Substance in the dose of 500 µg/kg body mass following the treatment plan:

First 2 days—4 injections daily (every 6 hours)
Days 3–10—3 injections daily (every 8 hours)
Days 11–13—2 injections daily (every 12 hours),
Days 14 and 15—1 daily injection.

All control group animals died at days 18–21 after infection with the clinical picture of distemper (neural form).

All experimental group animals survived: treatment with the substance completely protected animals from viral infection and also to decrease severity of the course of the infection. For instance, even by days 16–20 after the infection, treatment with the Substance led to significant improvement of general condition of the puppies, and starting with day 26 from the infection, the condition of the animals was evaluated as normal. A similar picture was observed during clinical trials of the Substance in dogs with distemper (250 animals of different breeds and ages), which were observed and treated at different veterinarian practices in Moscow and other cities in Russia: application of the Substance together with symptomatic treatment allowed to significantly decrease lethality and severity of distemper in different forms (subacute, intestinal, pulmonary, neural with initial symptoms, and neural with a marked convulsion syndrome) (Table 2. ).

TABLE 2

Efficacy of treatment (%) of different forms of distemper with the Substance.

| Clinical form of the disease | Subacute | Intestinal | Pulmonary | Neural, with initial symptoms | Neural, with a marked convulsion syndrome |
| --- | --- | --- | --- | --- | --- |
| Treatment without the substance | 70 | 50 | 50 | 10 | 10 |
| Treatment with the substance | 100 | 95 | 83 | 55 | 23 |

EXAMPLE 3

Therapeutic Activity of the Substance for Treatment of CVE

Efficacy of treatment of viral enterites of parvo-, rota-, and corona viral nature by the Substance in combination with symptomatic treatment was 90% (78 cases in dogs of different breeds and ages, observed and treated at veterinary practices in Moscow), whereas efficacy of treatment with standard symptomatic drugs does not exceed 50–60%. Treatment plan for the substance application in enterites is similar to that in distemper.

EXAMPLE 4

Therapeutic Activity of the Substance in CIH

Efficacy of treatment with the Substance in combination with symptomatic therapy was 95–100% (over 50 cases in dogs of different breeds and ages observed and treated at veterinary practices in Moscow). Treatment plan:

Day 1 (or first 2–3 days)—3 injections daily
Day 2 (or days 3–5)—2 injections daily
Day 3 (or days 5–7)—1 injection daily.

For the treatment of all above-mentioned viral infections in dogs the Substance was prescribed in the following doses:

0.1 ml for dogs with body mass under 1 kg
0.25 ml—1–5 kg
0.5 ml—5–10 kg
1.0 ml—10–20 kg
1.5 ml—20–30 kg
2.0 ml—30–45 kg

EXAMPLE 5

Therapeutic Activity of the Substance in FIE

Efficacy of the treatment with the Substance administered intramuscularly to the kittens less than 7 months of age diagnosed with panleukopenia (34 cases) was 100%. At the same time, efficacy of standard symptomatic treatment does not exceed 10%.

Treatment plan with the Substance in FIE: intramuscular injections of the preparation
Day 1—4 injections (with 4–6 hour intervals)
Day 2—3 injections (with 4–6 hour intervals)
Day 3—3 injections (with 4–6 hour intervals)
Days 4 through 6—2 injections (8 hour interval)

For treatment of cats the Substance was prescribed in following doses:
1. Intramuscular injections:
   0.2 ml for body mass under 1 kg
   0.5 ml for 2–5 kg
   1 ml for over 6 kg
2. Peroral administration:
   0.4 ml for body mass under 1 kg
   1 ml for 2–5 kg
   2 ml for over 6 kg

EXAMPLE 6

Therapeutic Activity of the Substance in FIR

Efficacy of treatment of 68 cats of different ages diagnosed with herpetic rhinotracheitis with the Substance (in combination with symptomatic therapy) was 95%. Efficacy of treatment under standard symptomatic treatment plan does not exceed 80%. The Substance was administered intramuscularly according to the plan provided in Example 4, and as applications onto virus-affected eye areas (2–3 times a day for 2–4 days).

EXAMPLE 7

Therapeutic Activity of the Substance in FIP

Efficacy of treatment of 12 kittens less than 4 months of age diagnosed with coronaviral peritonitis with the Substance (in combination with symptomatic therapy) was 50%. Efficacy of animal treatment with regular symptomatic medications does not exceed 1%. The Substance was applied according to the plan provided in Example 4.

EXAMPLE 8

Therapeutic Activity of the Substance in STG

Clinical trials of the Substance efficacy were carried out at the swine (breeding) facility "Krekshino", Naro-Fominsk Area, Moscow Region. Trials included 50 piglets with body mass less than 7 kg with laboratory-proven diagnosis of rotaviral gastroenteritis.

Twenty-five out of 50 animals were treated according to the standard symptomatic treatment plan; 25 experimental animals were treated, in addition to symptomatic medication, by intramuscular administration of 0.5 ml of the Substance according to the following plan:

| Days of disease | 1 | 2 | 3 | 4 | 5 | 6 | 7 |
|---|---|---|---|---|---|---|---|
| Number of injections per day | 4 | 3 | 3 | 3 | 2 | 2 | 1 |

Study results revealed that efficacy of treatment with the Substance reached 92% (23 animals completely recovered, 2 animals died), while in the control group treatment efficacy was only 40% (15 animals died, 10 recovered).

EXAMPLE 9

Activity of the Substance in ME

Line Balb/c mice with clinical picture of developed ectromelia (swollen faces, swollen eyelids and extremities, ulcerated tails) were subject to a one time intramuscular or intraperitoneal administration of the Substance in the dose of 500 $\mu$g/0.1 ml. Control group was treated with placebo. The animals were monitored for one month and longer.

In the group of sick mice treated with the Substance fast recovery was observed (on the average within 3–7 days), while in the control group 100% of mice died.

Therefore, the Substance has a high therapeutic activity in ectromelia.

EXAMPLE 10

The Substance Activity in MH

The trials were carried out on non-breed male mice, 10–12 g body mass. In the study, murine hepatitis virus strain Mesherin was used. The virus was introduced by two ways:

Intraperitoneally in a dose of 10 $LD_{50}$;
Perorally in the dose of 100 $LD_{50}$.

The substance was administered to the animals also in two ways:

Intramuscularly, 200 $\mu$g per mouse daily injections for 14 days after the infection;
Perorally, using similar plan.

Lethality percentages were calculated for control and experimental groups.

TABLE 3

Efficacy of murine hepatitis treatment with the Substance.

| Group name and # | Infection mode | Substance administration way | Lethality, % |
|---|---|---|---|
| 1. Control | Intraperitoneal | Not administered | 100 |
| 2. Control | Peroral | Not administered | 80 |
| 3. Experimental | Intraperitoneal | Intramuscular | 60 |
| 4. Experimental | Intraperitoneal | Peroral | 20 |

Data presented in Table 3 show that the Substance has a pronounced protective activity in murine hepatitis. For instance, its intramuscular administration led to 40% of animal survival rate, whereas no animals survived in control. Even more dramatic effect was achieved by peroral administration of the substance—80% of mice survived.

EXAMPLE 11

Substance Activity Against WEE (Western Equestrian Encephalomyelitis)

Strain California, studied in mice. Results show a high antiviral efficacy in the vivo experiment.

EXAMPLE 12

Substance Activity Against CMVI

In vivo studies on calves showed the substance was efficacious.

EXAMPLE 13

Substance Activity Against CL

In vitro studies on a CL-sensitive cell line showed about 50% protection.

EXAMPLE 14

Therapeutic Activity of the Substance Against RV

In vivo studies in mice showed therapeutic efficacy.

As illustrated by the following examples, the compositions of the invention are also effective in humans against diseases caused by viruses, such as for example, Human immunodeficiency (HIV), Herpes simplex, type 1 (HSV-1), Measles (MV), Parotitis (PV), Hepatitis A (HAV), Tick-borne encephalitis (TBE), Yellow fever (YFV), and Influenza (IV).

EXAMPLE 15

Antiviral Activity of the Substance in HIV, HSV-1, MV, PV, and HAV

In vivo studies in a murine model (HSV) and in vitro studies (all other viruses) showed antiviral activity of the substance.

EXAMPLE 16

Therapeutic Activity of the Substance Against TBE, YFV, and IV

In vivo studies in mice showed a pronounced protective effect of the substance.

As illustrated by the following example, the compositions of the invention are also effective for Preventing of Viral Infections.

EXAMPLE 17

The Substance was tested as preventative for the decrease of risk of the development of viral infections in dogs (distemper, enteritis, hepatitis) and cats (panleucopenia, rhinotracheitis, coronaviral enteritis, peritonitis). The Substance was found to be effective as preventative agent.

As illustrated by the following examples, the compositions of the invention are also effective for the Enhancement of Vaccination Efficacy.

EXAMPLE 18

Correction of Secondary Immune Deficiencies Induced by Different Enviornmental Factors: Viral Infection, Stress and Radiation in Mice Results show that the Substance possesses a strong immune corrective activity (independent of the nature of the factor) and can restore functions of the immune system.

As illustrated by the following example, the compositions of the invention are also effective as an Immunocorrective agent.

EXAMPLE 19

Use as a Stimulator of Factors of Natural Body Resistance: Interleukins (IL), Interferons (IFN), Tumor Necrosis Factor (TNF)

Results are shown in the following table.

| Cause of secondary immune deficiency (SID) | Characteristics of SID | Effect of Substance |
|---|---|---|
| Tachiny virus | Supression of antibody producing cells (APC), type B 2.5 fold | 100% restoration of APC function |
| Prolonged hypokinesia | Supression of APC functions 12-fold | 97% restoration of APC function |
| Irradiation (900 rad) | Death of 20% of animals in 30 days after impact. Inhibition of bone marrow stem cell proliferation | IM administration led to a 50% increase in survival, normalization of bone marrow stem cell proliferation |

EXAMPLE 20

Use of the Substance as a Stimulator of Body Natural Resistance Factors: Interleukins (IL), Interferons (IFN), Tumor Necrosis Factor (TNF)

In mice, the substance showed TNF increase in 1 h and 2 days; IL-1 increase after 24 h, and IFN increase in blood serum between 2 and 72 h.

As illustrated by the following example, the compositions of the invention also promote wound healing.

EXAMPLE 21

In Vivo Studies in Guinea Pigs Showed Efficacy of the Substance for the Promotion of Wound Healing The Substance was used to treat guinea pigs with aceptic wounds on skin of the right hind thigh by cutting skin patch 1 cm in diameter. Each group consisted of 4 animals.
Group 1 was treated with erythromycin ointment
Group 2 was treated with 5% ACTOVEGIN ointment
Group 4 received placebo (50% lanolin solution)
Group 4 was treated with the Substance (0.4% solution in 50% lanolin).

Wound size was imprinted daily on a cellophane film, the imprints were cut out and weighted. Dynamics (weight in mg) is shown in the following table.

| Group | 0 day | 1 day | 2 days | 5 days | 8 days |
|---|---|---|---|---|---|
| 1 | 8.5 | 7.75 | 8.85 | 10 | 5.25 |
| 2 | 9.1 | 7.6 | 7.67 | 8.3 | 5 |
| 3 | 6.33 | 5.66 | 6.33 | 5.66 | 5.5 |
| 4 | 9 | 4.33 | 4.33 | 3 | 2.66 |

EXAMPLE 22

Assessed Hemoglobin Content of Blood in Calves Infected with CMVI

As illustrated by the following example, the compositions of the invention are also effective as antitumor agents.

EXAMPLE 23

Studied by Measuring of Induced Tumor Sizes in Mice with Melanoma B-16 or Lewis Lung Carcinoma. Showed Antitumor Activity of the Substance As illustrated by the following example, the compositions of the invention are also possess hepatoprotective activity.

EXAMPLE 24

Studies in Green Monkeys with Worm Invasion in Liver Showed Hepatoprotective Activity The data from the above examples demonstrates that a representative composition of the invention has significant antiviral activity in infections of humans and animals (including threatening infections in humans caused by HIV, rabies and tick-borne encephalitis viruses), is a highly efficient preventative substance, is effective to increases vaccination efficacy, stimulates body natural resistance factors, is a good immunocorrector, normalizes physiological parameters of the body, speeds up wound healing, has an antitumor activity, and has hepatoprotective activity.

EXAMPLE 25

Studies in Mice Infected with Type A Influenza Virus

Experiments were carried out on mice, Line C57B1/6, intranasally infected with the Type A Influenza Virus (H1N1), strain WSN in the dose of 5 $LD_{50}$. Simultaneously with the infection, a single dose of polyprenol monophosphate, or polyprenol monophosphate with polyprenol polyphosphate (97:3, w/w) as 0.4% solution in the dose of 5 ug per mouse was administered.

Average life span of the animals, treated with polyprenol monophosphate, was 6.6 days, animals treated with polyprenol monophosphate with polyprenol polyphosphate lived 8.7 days. This shows a higher efficacy of polyprenol monophosphate with polyprenol polyphosphate compared to polyprenol monophosphate.

EXAMPLE 26

The substance induces in vitro biosynthesis of mRNA of cytokines IL-1, IL-2, i.e. the cascade characteristic of the Th1 immune response and inhibits constitutive biosynthesis of mRNA of tumor necrosis factor (TNF).

The method of screening for substance activity was based in the assessment of the induction of interferon biosynthesis in vivo. Therefore, the substances were classified as interferon inducers.

The in vitro effects of the substance on the induction of mRNA biosynthesis for a number of cytokines was studied. The method of research was RT-PCR. Treatment of cell cultures with the preparations led to the induction of biosynthesis of mRNAs for IL-1 and IL-2. The profile of cytokine response points out to the involvement of the Th1 type immune system in response to the treatment.

Research was carried out in human osteogenic hypotriploid sarcoma cell line MG-63 (ATCC CRL-1427), which has a constitutive production of interferon alpha (IFN). The cells were grown in Eagle Minimal Eagle Medium (MEM) supplemented with 2 mM glutamine and Earle BSS (1.5 g/l sodium bicarbonate, 0.1 mM non-essential aminoacids, 1.0 mM sodium piruvate, and 10% fetel bovine serum).

The substance was introduced into culture media in the final concentrations of 200 and 250 g/ml, respectively. The cells were harvested at 2, 24, 48, and 72 h after induction, and total RNA was isolated using Rneasy Total RNA kit (Qiagen, Santa Clara, Calif.). RNA concentration was measured in total RNA preparations, and cDNA was synthesized from 2.0 g total RNA using oligo dT primers and AMV reverse transcriptase (both from New England Biolabs, Bedford, Mass.). Equalized amounts of cDNA were used as templates for PCR reactions with the primer pairs specific to IFN, IFN, IL-1, IL-2, IL-4, IL-6, IL-10, TNF, and actin (served as control). Thermal cycling procedure included 2 min at 94 C., 35 cycles of 1 min at 94 C., 2 min at 55 C., and 2 min at 72 C., followed by 5 min at 72 C. PCR products were resolved by electrophoresis in 3% agarose gels.

The Substance induced biosynthesis of IL-1 and IL-2 mRNA. The cell line expressed IFN and TNF mRNA constututively, at high levels. No mRNA induction was observed for IFN, IL-4, IL-6 or IL-10. The highest levels of IL-1 mRNA were observed at 2 and 24 h after the induction and decreased after 48 h after induction. IL-2 mRNA biosynthesis was at its peak at 24 and 48 h after the induction. The substance inhibited constitutive expression of TNF mRNA.

These results suggest that (1) immune system is a target for action of the Substance; (2) treatment of cells with the Substance leads to the induction of transcription of the Th1 cytokine mRNA (IL-1, IL-2) and can also inhibit transcription of TNF mRNA; (3) biological activity of the the Substance is due to the upregulation of Th1 type immune response.

These results of the above examples show that a representative compositions of the invention is useful to provide antiviral response induction and neoplastic development inhibition. The compositions of the invention may be particularly useful for the treatment of viruses that naturally induce Th1 immune response.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A pharmaceutical composition comprising a pharmaceutically acceptable carrier, and a therapeutically effective amount of a combination of 1) isolated polyprenol monophosphates of the formula H—[—CH$_2$—C(CH$_3$)=CH—CH$_2$]n-O—P(=O)(OH)$_2$ wherein n is an integer from 6–19 inclusive, or a salt thereof, and 2) isolated polyprenol pyrophosphates of the formula H—[—CH$_2$—C(CH$_3$)=CH—CH$_2$]$_m$—O—P(=O)(OH)—O—P(=O)(OH)$_2$ wherein m is an integer from 6–19 inclusive, or a salt thereof.

2. The composition of claim 1 wherein n is 9, 10, 11, 12, 13, or 14 in greater than 50% of the polyprenol monophosphates.

3. The composition of claim 1 wherein m is 9, 10, 11, 12, 13, or 14 in greater than 50% of the polyprenol pyrophosphates.

4. The composition of claim 1 wherein the weight percent of polyprenol monophosphates is greater than the weight percent of the polyprenol pyrophosphates.

5. The composition of claim 1 wherein the weight percent of polyprenol monophosphates is not more than about 2 times greater than the weight percent of the polyprenol pyrophosphates.

6. The composition of claim 1 wherein the weight percent of polyprenol monophosphates is not more than about 4 times greater than the weight percent of the polyprenol pyrophosphates.

7. The composition of claim 1 wherein the weight percent of polyprenol monophosphates is not more than about 5 times greater than the weight percent of the polyprenol pyrophosphates.

8. The composition of claim 1 wherein the weight percent of polyprenol monophosphates is not more than about 10 times greater than the weight percent of the polyprenol pyrophosphates.

9. The composition of claim 1 wherein the weight percent of polyprenol monophosphates is not more than about 20 times greater than the weight percent of the polyprenol pyrophosphates.

10. The composition of claim 1 wherein n is 11 in at least 80% of the polyprenol monophosphates present.

11. The composition of claim 1 wherein m is 11 in at least 80% of the polyprenol pyrophosphates present.

12. The composition of claim 10 wherein m is 11 in at least 80% of the polyprenol pyrophosphates present.

13. The composition of claim 12 wherein the weight percent of polyprenol monophosphates is about 10 times greater than the weight percent of the polyprenol pyrophosphates.

14. A pharmaceutical composition comprising a pharmaceutically acceptable carrier, and a therapeutically effective amount of isolated polyprenol pyrophosphates of the formula H—[—CH2-C(CH$_3$)=CH—CH$_2$]$_m$—O—P(=O)(OH)—O—P(=O)(OH)$_2$ wherein m is an integer from 6–19 inclusive, or a salt thereof.

15. The composition of claim 14 wherein m is 9, 10, 11, 12, 13, or 14 in greater than 50% of the polyprenol pyrophosphates.

16. The composition of claim 14 wherein m is 11 in at least 80% of the polyprenol pyrophosphates present.

17. A method for producing an antiviral effect in an animal comprising administering to an animal in need of such treatment, an effective antiviral amount of a composition of claim 1 or 14.

18. A method for modulating the immune system of an animal comprising administering to an animal in need of such treatment, an effective immunomodulatory amount of a composition of claim 1 or 14.

19. A method for the treatment of distemper virus (DV), canine enteritis (parvo, rota, and corona viruses; CEV), canine infectious hepatitis (CIH), feline infectious gastroenteritis (panleukopenia, FIE), feline infectious rhinotracheitis (agent—herpes virus; FIR), feline infectious enteritis and peritonitis (agent—corona virus, FIP), swine transmissive gastroenteritis (agent—rotavirus; STG), murine ectromelia (ME), cattle leukemia (CL), calf mixed viral infection (agents—parvo, adeno, and corona viruses; CMVI), western equestrian encephalomyelitis (WEE), or rabies (RV), comprising administering to an animal in need of such treatment, an effective therapeutic amount of a composition of claim 1 or 14.

20. A method for upregulating Th1 related immunity in an animal comprising administering to an animal in need of such treatment, an effective amount of a composition of claim 1 or 14.

21. A method for enhancing the protective effects of a vaccine comprising administering the vaccine to an animal in need of such treatment in combination with a composition of claim 1 or 14.

22. A method to correct an individual immune system comprising administering to an animal in need of such treatment, an effective amount of a composition of claim 1 or 14.

* * * * *

UNITED STATES PATENT AND TRADEMARK OFFICE
CERTIFICATE OF CORRECTION

PATENT NO. : 6,525,035 B1
DATED : February 25, 2003
INVENTOR(S) : Leonid L. Danilov et al.

It is certified that error appears in the above-identified patent and that said Letters Patent is hereby corrected as shown below:

<u>Title page,</u>
Item [56], References Cited, FOREIGN PATENT DOCUMENTS, delete
"A61K/34/045" and insert -- A61K/31/045 -- therefor.
Insert -- ......... A61/31/21 -- after "10/1991".
Item [57], ABSTRACT,
Line 2, delete "H—[—CH2-C(CH3)=CH—CH2]n-O—P(=O)(OH)2" and insert
-- H—[—$CH_2$-C($CH_3$)=CH—$CH_2$]n-O—P(=O)(OH)$_2$ -- therefor.
Line 5, delete "H—[—CH2-C($CH_3$)" and insert -- H—[—$CH_2$-C($CH_3$) -- therefor.

<u>Column 18,</u>
Line 16, delete "H—[—CH2-C($CH_3$)" and insert -- H—[—$CH_2$-C($CH_3$) -- therefor.

Signed and Sealed this

Ninth Day of September, 2003

JAMES E. ROGAN
*Director of the United States Patent and Trademark Office*